(12) United States Patent
Morgan et al.

(10) Patent No.: US 9,448,200 B2
(45) Date of Patent: Sep. 20, 2016

(54) PROCESS FOR SENSING AT LEAST ONE PARAMETER IN WATER

(71) Applicant: University of Southampton, Southampton (GB)

(72) Inventors: Hywel Morgan, Southampton (GB); Matthew Charles Mowlem, Southampton (GB); Xi Huang, Southampton (GB); Robin William Pascal, Southampton (GB)

(73) Assignee: University of Southampton, Southampton (GB)

( * ) Notice: Subject to any disclaimer, the term of this patent is extended or adjusted under 35 U.S.C. 154(b) by 0 days.

(21) Appl. No.: 14/392,031

(22) PCT Filed: Sep. 19, 2013

(86) PCT No.: PCT/GB2013/000391
§ 371 (c)(1),
(2) Date: Mar. 18, 2015

(87) PCT Pub. No.: WO2014/044998
PCT Pub. Date: Mar. 27, 2014

(65) Prior Publication Data
US 2015/0212040 A1    Jul. 30, 2015

(30) Foreign Application Priority Data
Sep. 20, 2012  (GB) .................................. 1216859.7

(51) Int. Cl.
| | |
|---|---|
| *G01N 27/327* | (2006.01) |
| *G01N 27/416* | (2006.01) |
| *G01N 27/49* | (2006.01) |
| *G01N 33/18* | (2006.01) |

(52) U.S. Cl.
CPC .......... *G01N 27/4163* (2013.01); *G01N 27/49* (2013.01); *G01N 33/18* (2013.01)

(58) Field of Classification Search
CPC ............. G01N 27/4163; G01N 27/49; G01N 27/404; G01N 27/48; G01N 33/18
See application file for complete search history.

(56) References Cited

U.S. PATENT DOCUMENTS

| | | | |
|---|---|---|---|
| 6,428,684 | B1 | 8/2002 | Warburton |
| 2008/0202944 | A1 | 8/2008 | Santoli et al. |
| 2015/0192534 | A1 | 7/2015 | Morgan et al. |
| 2015/0192535 | A1 | 7/2015 | Morgan et al. |
| 2015/0226697 | A1 | 8/2015 | Morgan et al. |

FOREIGN PATENT DOCUMENTS

JP    2001 174436 A    6/2001

OTHER PUBLICATIONS

Machine translation of JP H11-183464, Abstract Only, Jul. 1999.*
"Monitor CTD+", http://www.valeport.co.uk/Portals/0/Docs/Datasheets/Valeport_MonitorCTD_plus_v2a.pdf, Feb. 2011, 1 page.

* cited by examiner

*Primary Examiner* — J. Christopher Ball
(74) *Attorney, Agent, or Firm* — Iandiorio Teska & Coleman, LLP

(57) ABSTRACT

Apparatus (2) for sensing at least one parameter in water, which apparatus (2) comprises: (i) a dissolved oxygen sensor (4) for sensing dissolved oxygen in the water; and which apparatus (2) is such that: (ii) the dissolved oxygen sensor (4) has a working electrode and a reference electrode; and (iii) a voltage signal is applied between the working electrode and the reference electrode, and the voltage signal provides a conditioning waveform, then a wait time, and then a measurement function.

5 Claims, 12 Drawing Sheets

| Diameter (mm) | 10 | 20 | 40 | 100 | 200 |
|---|---|---|---|---|---|
| Cell A | 709.6 (43.3%) | 504.4 (1.88%) | 496.1 (0.20%) | 495.1 (0.00%) | 495.1 (0%) |
| Cell B | Infinite | 1593.6 (0.95%) | 1580.3 (0.11%) | 1578.7 (0.01%) | 1578.6 (0.00%) |
| Cell C | 662.3 (4.44%) | 634.9 (0.13%) | 634.1 (0.00%) | 634.1 (0.00%) | 634.1 (0.00%) |
| Cell D | 677.5 (1.42%) | 668.4 (0.07%) | 668.0 (0.00%) | 668.0 (0.00%) | 668.0 (0.00%) |

Resistance ($\Omega$) (error compared with diameter = 200 mm)

FIG. 7C

PROCESS FOR SENSING AT LEAST ONE PARAMETER IN WATER

This invention relates to a process for sensing at least one parameter in water. The sensed parameter may be one or more of conductivity, temperature, and dissolved oxygen.

Apparatus for sensing conductivity, temperature, and depth is a requirement for determining the physical properties of sea water and are frequently used to determine the practical salinity which in turn can be used to estimate density or composition. The practical salinity of ocean water typically ranges from 33 to 37, but can be as low as 0.5 in Brackish seas. Salinity >300 is possible in landlocked water bodies. Salinity varies with both depth (non-linearly, but typically decreases by 2 descending the first 1000 m) and location. Although some applications need an accuracy of 0.001, a typical accuracy requirement for satellite oceanographic applications is about 0.1, which requires conductivity and temperature accuracies to be 0.1 mS/cm and 0.1° C. However, most oceanographic data requires an accuracy in salinity of 0.01. In addition to sea water applications, sensing conductivity is also important for freshwater. For example, river water has a normal conductivity range of 50~1500 µS/cm; freshwater fish prefer a conductivity between 150~500 µS/cm; typical drinking water is in the range of 50~500 µS/cm; and industry waters can range to as high as 10 mS/cm. Therefore monitoring the conductivity of freshwater is extremely important for water the industry and aquaculture. Several high accuracy types of apparatus for sensing conductivity, temperature and depth are commercially available but they are large and power hungry, and this precludes their use in applications requiring miniaturisation and long-term operation. Small data storage tags have been developed to measure temperature and salinity. However these do not make high accuracy conductivity measurements.

The measurement of dissolved oxygen concentration or partial pressure in water is required for a wide range of industrial and environmental applications. This includes, for example, the control of aeration in sewage water treatment, assessment of eutrophication, study of respiration, hypoxia, and primary production in natural waters. Oxygen can be measured with Clark electrodes including adaptions for low concentrations and adaptions that have been microfabricated. The use of optical indicators known as optodes is also widespread in many applications. A miniaturised analytical system is known that automates Winkler titration in situ. This requires storage of reagents and separate systems for fluid actuation, fluid handling and optical detection but has good performance (precision of 0.3% relative standard deviation). Recessed disc mircoelectrodes operated at steady state current have also been used widely for determination of dissolved oxygen in life sciences, and for stripping voltammetry detection of heavy metals, The microfabrication of micro electro-mechanical systems (MEMS) microsensors is established for recessed ring type microelectrodes operated at steady state current.

Each of the above mentioned existing technologies has different limitations. Optodes suffer from a slow response time ($T_{90}$~30 s) and are difficult to manufacture in high volume and low cost. Clark electrodes are relatively complex to fabricate, are fragile, often flow sensitive and require regular recalibration. Reagent-based systems are complex with effects on durability and cost. Recessed bare disc microelectrodes manufactured from gold wire or amalgam deposited into tapered glass or polymer have poor long-term performance in natural waters unless tipped with a membrane (which negatively impacts sensitivity, time response, and stability), and are fragile and difficult to mass-manufacture. Known microfabricated MEMS microelectrodes are needle type making them extremely fragile. The manufacturing process for the microfabricated MEMS also requires precision dicing, deposition and etching (including in hydrofluoric acid) in three dimensions, and is difficult to automate for mass production.

Biofouling of sensors is a widely encountered and negatively impacts long-term performance. For example diffusion through fouled membranes is restricted, which can affect sensitivity and time response in electrochemical or analyte consumptive sensors. Strategies to mitigate or reduce biofouling include the use of copper, non-stick materials, mechanical wipers, biocide materials, surface texturing, natural products, and artificially stimulated quorum sensing. Electric fields and electrochemically generated chemical environments (e.g. generation of copper and chlorine ions) have also been applied using electrode structures incorporated into the device or monitoring system solely for this purpose. The electrochemical generation of chlorine and hence hypochloric and hydrochloric acid in marine environments is well established for biofouling reduction. To date this has been applied by use of electrode structures external to the sensor transducer. The technique has also been applied using a large scale electrode mesh around but not fabricated upon the optical window of in situ optical sensors.

It is an aim of the present invention to alleviate at least one of the above mentioned problems.

Accordingly, the present invention provides a process for sensing at least one parameter in water, which process comprises:
  providing in the water apparatus comprising a dissolved oxygen sensor which is for sensing dissolved oxygen in the water and which
  has a working electrode and a reference electrode; and
  (ii) applying a voltage signal between the working electrode and the reference electrode, and such that the voltage signal provides a conditioning waveform, then a wait time that returns a perturbed local oxygen concentration at the working electrode to a bulk oxygen concentration value, and then a measurement function that is sufficiently short that the extent of a depleted oxygen zone at the working electrode is minimised, and hence sensitivity to flow is minimised.

The process of the present invention is advantageous in that the conditioning waveform is able to ensure that the apparatus operates with correct voltages, frequencies etc. The conditioning waveform enables the electrode to sense the dissolved oxygen. The conditioning waveform and the wait time work together to ensure the precise and accurate functioning of the apparatus.

The apparatus may be one in which the dissolved oxygen sensor includes an auxiliary electrode, and in which the voltage between the working electrode and the auxiliary electrode is set such that the desired voltage between the working electrode and the reference electrode is attained.

The apparatus may be one in which the conditioning waveform duration is 100 ms-800 ms.

The apparatus may be one in which the post conditioning waveform delay is 200 ms-1800 ms.

The apparatus may include a depth sensor for sensing the depth of the water. Preferably the depth sensor is on the same substrate as the dissolved oxygen sensor but it may be on a different substrate if desired.

The apparatus may reduce cost of manufacture through the use of planar fabrication. The apparatus may increase the frequency of valid measurements, and may be flow insensitive and stable. The apparatus may use an array of bare disc platinum microelectrodes with recesses for measuring dissolved oxygen. The principle function of each these recesses is to reduce flow sensitivity. The microelectrode array can be interrogated with all electrodes in parallel to increase signal magnitude and hence performance, or addressed sequentially or individually to further increase the frequency of valid measurements and/or sensor lifetime. The apparatus may be able to use packaged electronics. The apparatus may be able to use a waveform which maximises performance, long term stability, and flow insensitivity.

The apparatus may be able to achieve antifouling by the electrochemical generation of chlorine. In addition and advantageously, the apparatus may be able to electrochemically generate oxygen. The apparatus of the present invention may be able to use sensor electrodes which are sufficiently robust that they can be used as the electrodes for the generation of these reactive species. Hitherto known apparatus has used electrodes on or in the vicinity of a sensing area and that have no function in transduction. The apparatus may also do this, but with the additional advantage that biofouling reduction electrodes can be created using the same manufacturing process as for the sensing electrodes, rather than by using additional processes as currently occurs with known apparatus. The apparatus may use small size sensors, and their electrodes may cover a large area of a substrate surface. The small size limits the current, and hence power used when generating oxygen and chlorine. The large coverage limits the required duration of reactive species generation, because a high concentration can be achieved quickly in a thin layer covering the sensor. If as in known apparatus, the reactive species generating electrodes are distant from the sensor then diffusion and convection must transport these species to the site of transduction. This inevitably results in a lower concentration at the sensor than at the site of generation.

Embodiments of the invention will now be described solely by way of example and with reference to the accompanying drawings in which.

Figure 7A:
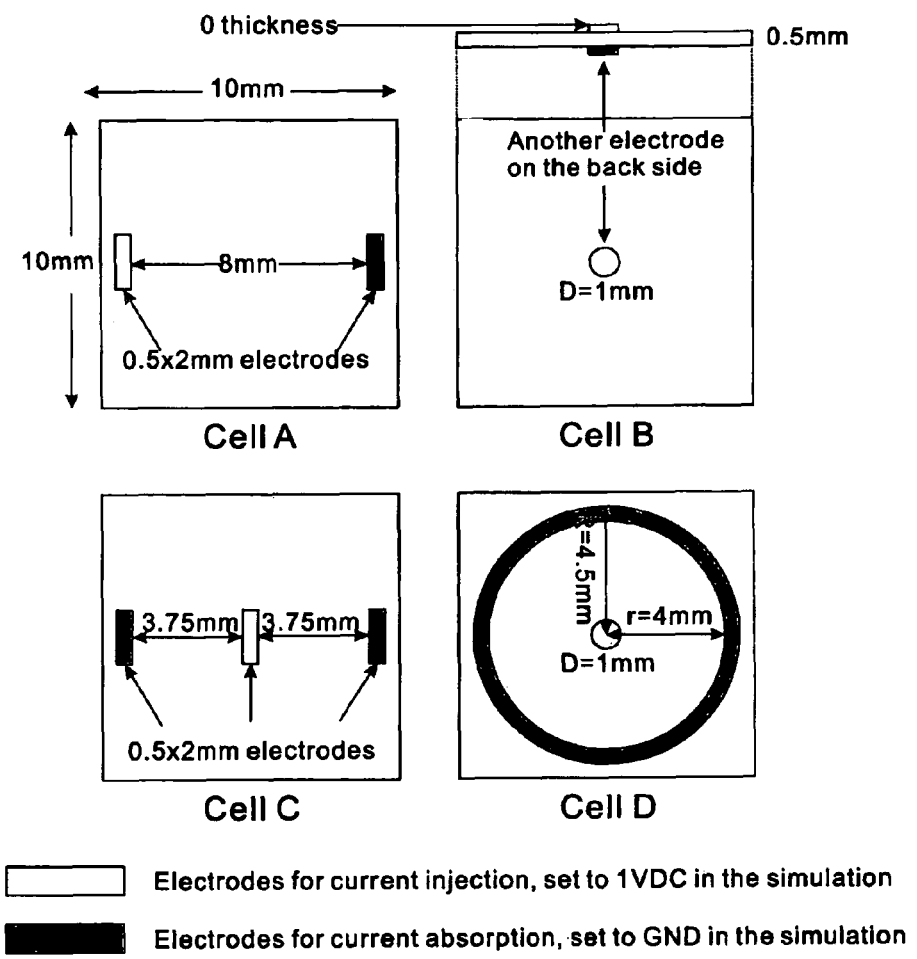
FIG. 7a shows four different open conductivity cells.
Figure 7B:
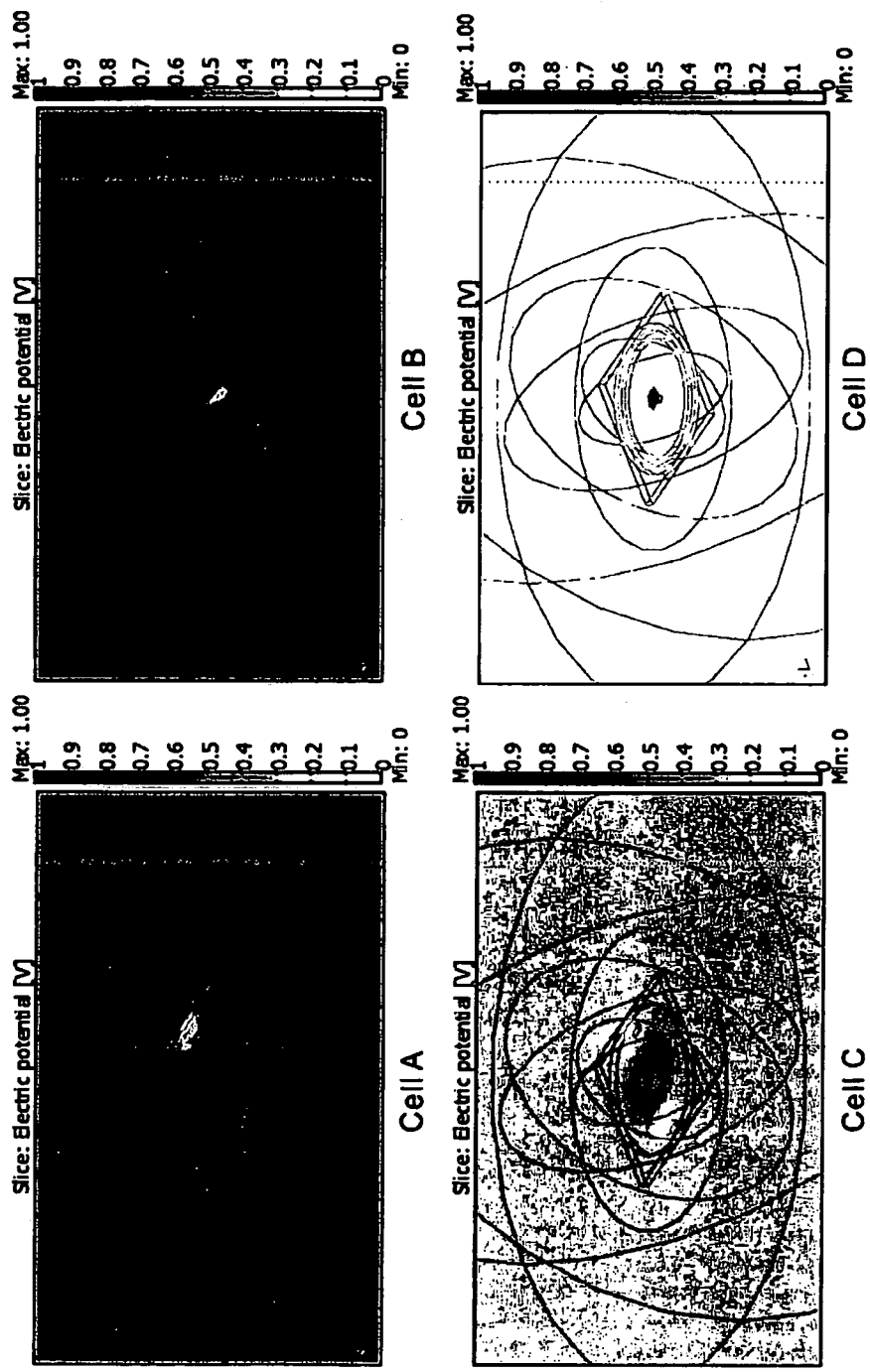
Figure 8:
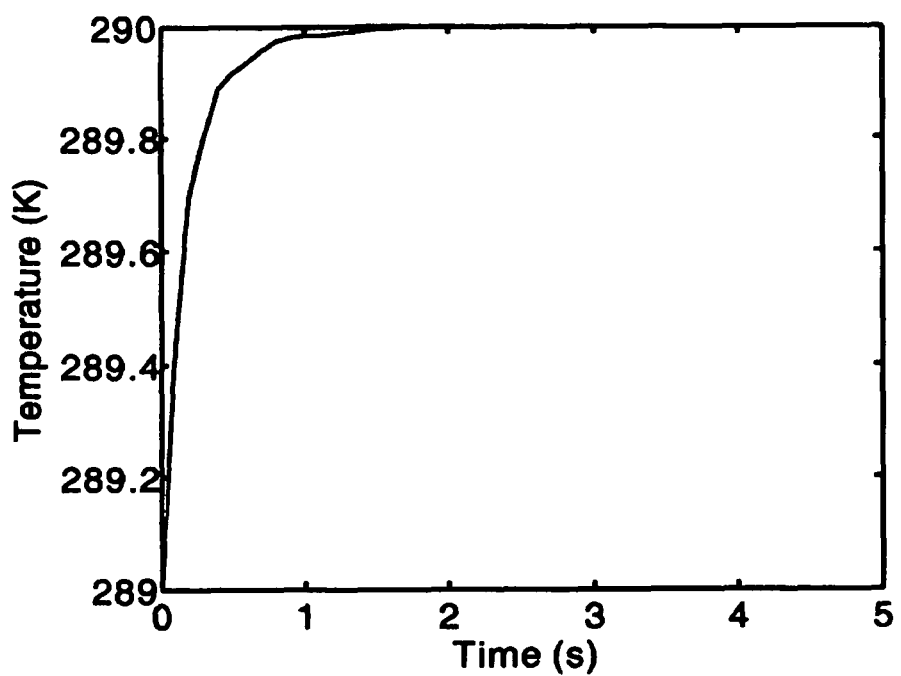
Figure 9:
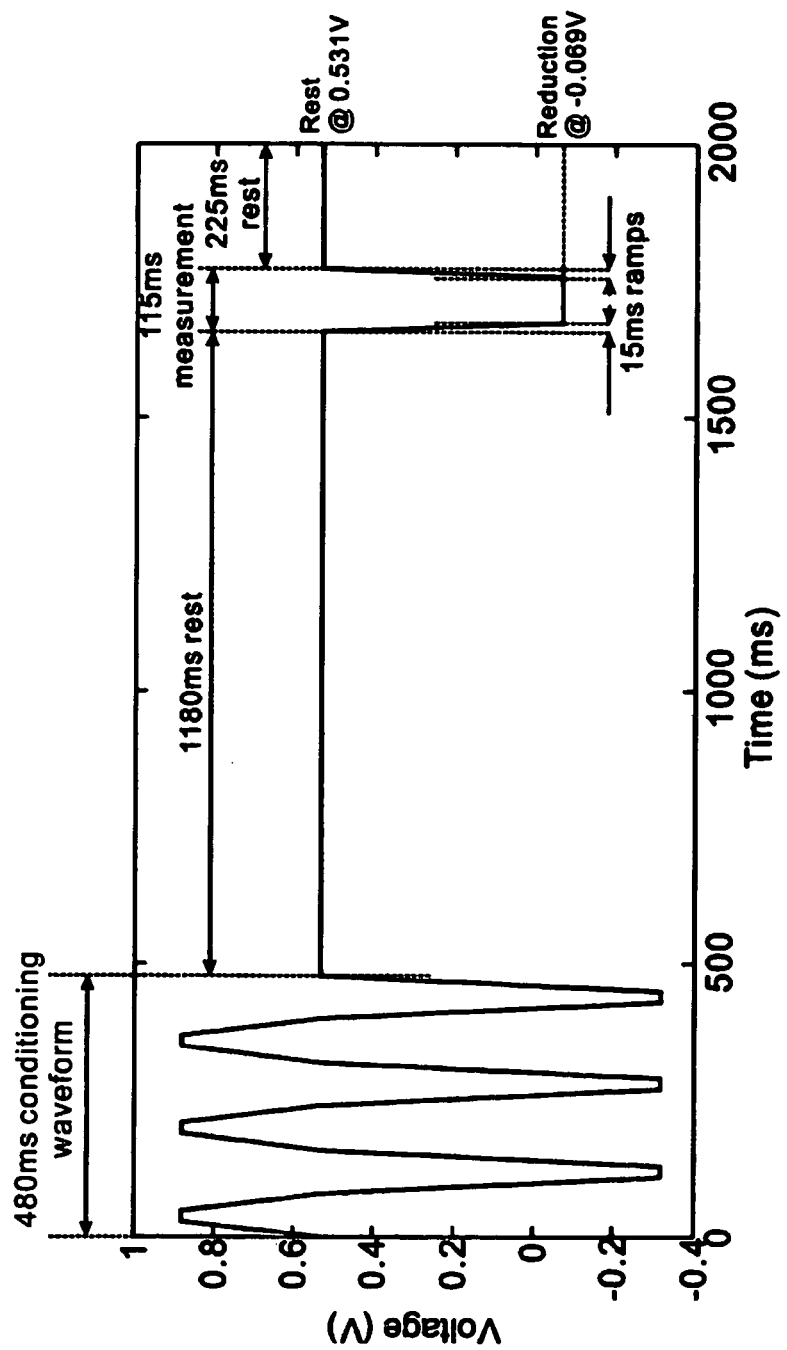
Figure 10:
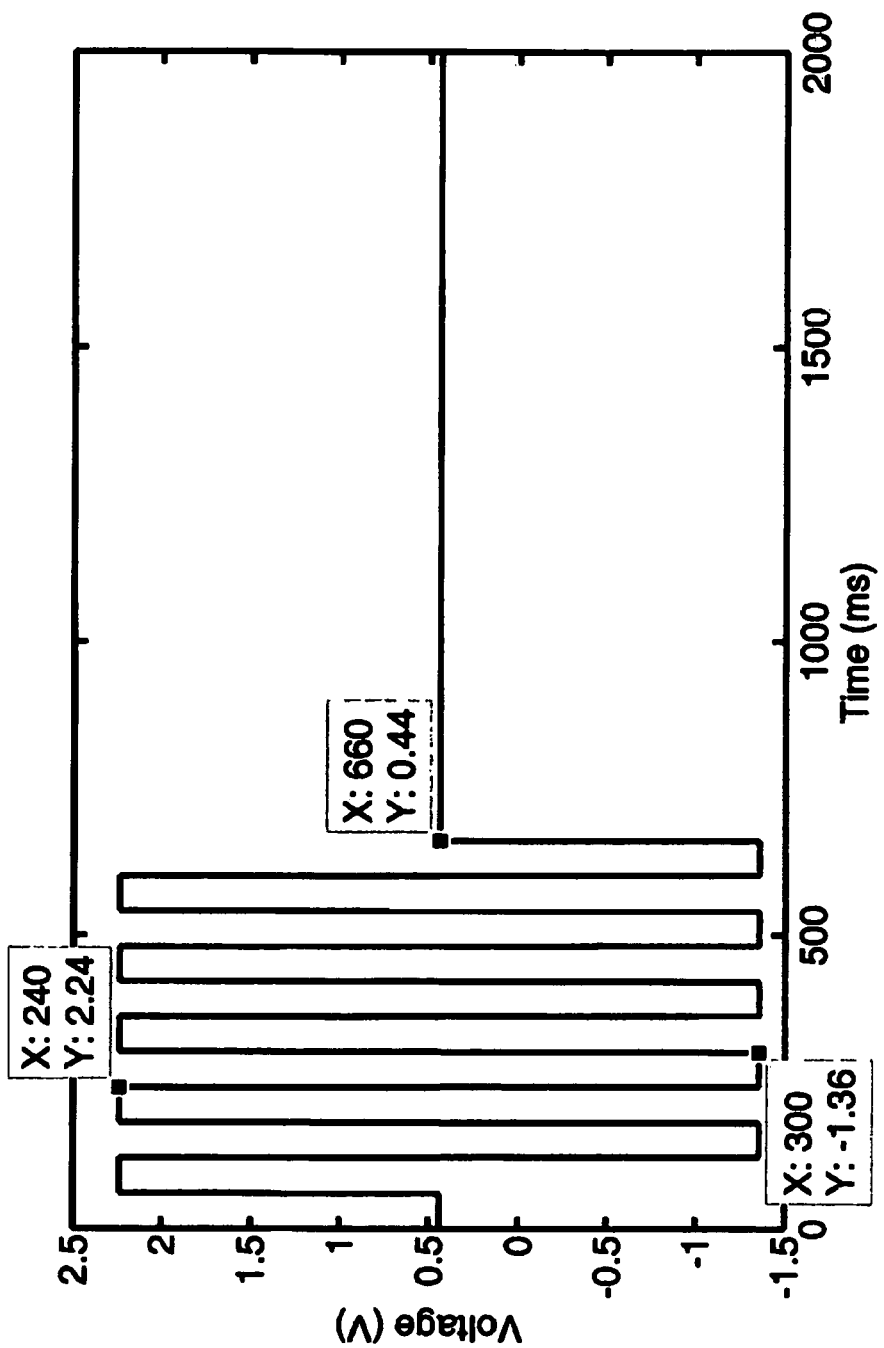

FIG. 7b compares the electrical field and potential for the different cells shown in FIG. 7a;

FIG. 7c is a table summarising resistance errors achieved by the conductivity cells shown in FIG. 7a;

FIG. 8 show results of finite element model (FEM) of the average temperature change of a platinum resistance ther-
mometer (PRT) in flowing water, when water temperature is 1 K higher and sensor head is 6 mm high;

FIG. 9 shows the voltage waveform applied to a working electrode for conditioning and measurement; and FIG. 10 shows an antifouling waveform applied to sensing electrodes.

APPARATUS FOR SENSING DISSOLVED OXYGEN IN WATER, AND OPTIONALLY ALSO SENSING CONDUCTIVITY IN WATER. ALSO PRODUCING APPARATUS FOR SENSING DISSOLVED OXYGEN IN WATER BY MICROFABRICATION ON A LAMINAR SUBSTRATE

Figure 1:
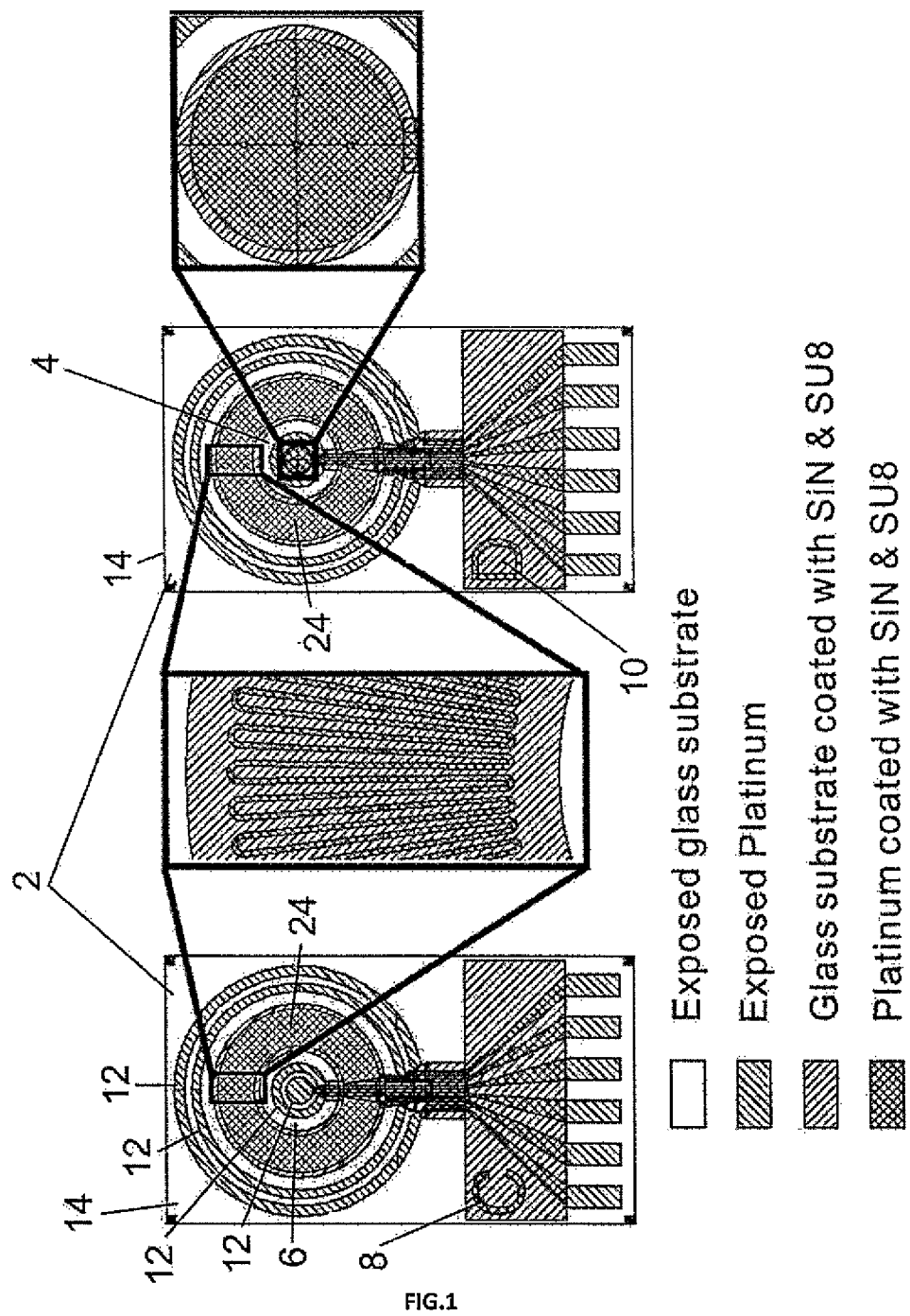
FIG. 1 shows part of the apparatus for sensing at least two parameters in water, namely conductivity and dissolved oxygen, and also temperature, the apparatus comprising a sensor head and packaged electronics, and FIG. 1 showing two sides of a chip used in the sensor head.

FIG. 1 shows apparatus 2 for sensing at least one parameter in water. More specifically, FIG. 1 shows apparatus 2 for sensing dissolved oxygen in water. The apparatus 2 comprises a dissolved oxygen sensor 4.

The apparatus 2 shown in FIG. 1 is such that it is also able to sense a second parameter, namely conductivity in the water. The apparatus 2 also comprises a conductivity sensor 6.

The apparatus 2 shown in FIG. 1 is also such that the dissolved oxygen sensor 4 is able to be produced by fabrication on a laminar substrate in the form of a chip. The fabrication may be regarded as microfabrication.

The apparatus 2 shown in FIG. 1 comprises a sensor head which may be used together with suitably packaged electronics. FIG. 1 shows two sides 8, 10 of a chip used in the sensor head. The left side 8 of FIG. 1 shows a layout for sensing the conductivity, and the right side 10 of FIG. 1 shows a layout for sensing the dissolved oxygen.

Figure 2:
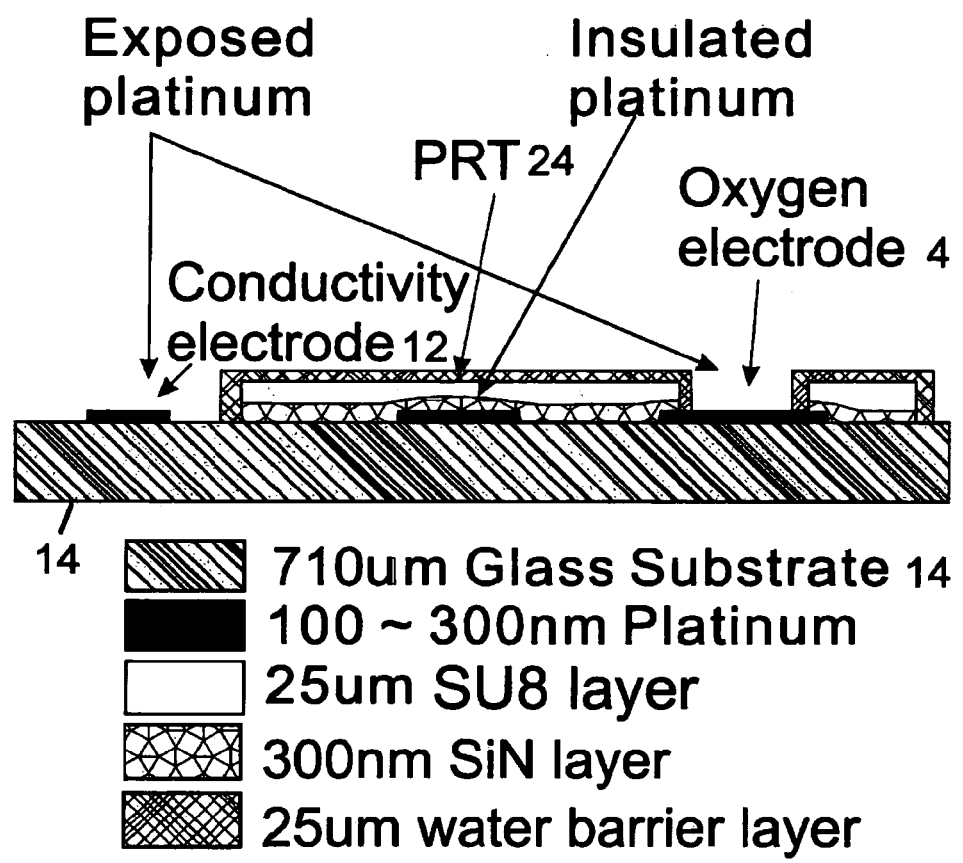
FIG. 2 is a diagram of sensor chip structure with a 710 μm thick glass substrate, a (100~300 nm) platinum layer, SiN and SUB insulating layers, and a water barrier layer.
Figure 3:
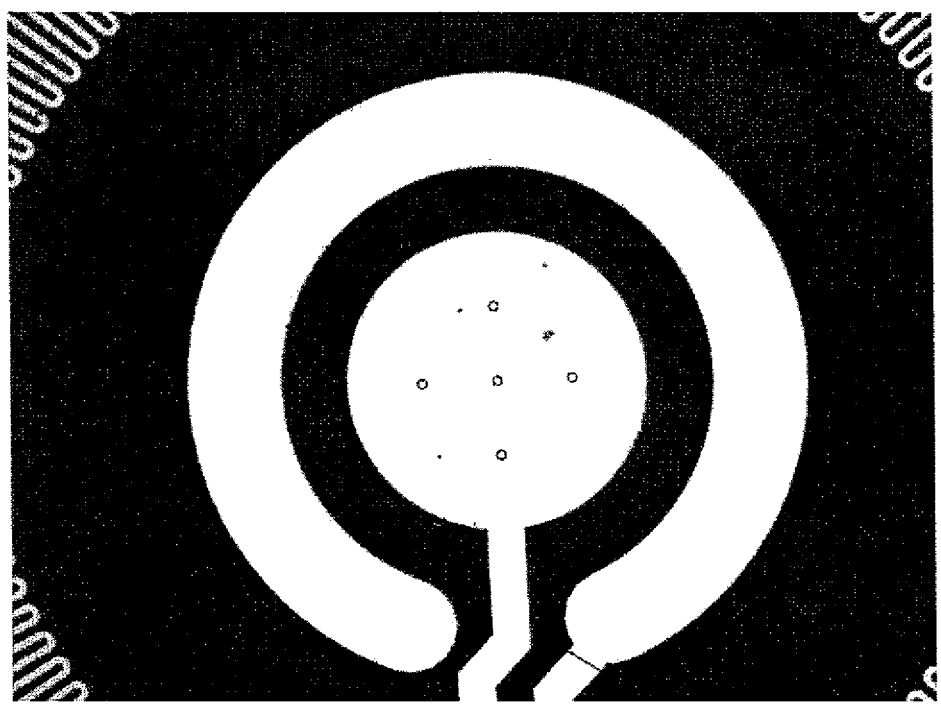
FIG. 3 shows an optical microscopy image of five 25 μm recessed bare platinum oxygen electrodes forming an oxygen sensor array.

FIG. 2 is an illustrative schematic of a cross section of the chip shown in FIG. 1 and in the region of the microelectrodes. To fabricate the chip, electrodes were deposited onto 710 μm thick 6" diameter glass wafers by sputtering Ti and Pt. The microelectrodes were then shaped by conventional photolithography and ion beam milling. A 300 nm layer of SiN was then deposited over the entire wafer, followed by 25 μm layer of an epoxy-based negative photoresist known as SU8. The SU8 was exposed and developed through a photomask to open windows in specific locations on the central working electrode for the dissolved oxygen sensor, and the conductivity electrodes. The SiN in these exposed areas was then dry etched to expose bare platinum, thus forming exposed conductivity electrodes 12 and an array of recessed microelectrodes 14 for oxygen sensing, as shown in FIG. 2 and FIG. 3. In order to insulate the SU8 from water uptake, a hydrophobic polymer was deposited and patterned to expose platinum for the conductivity and dissolved oxygen, sensors. Individual chips were cut from the 6" wafer by scribing and dicing.

In the embodiment shown in FIG. 1, the apparatus 2 with the dissolved oxygen sensor 4 and the conductivity sensor 6 comprises a glass substrate onto which are microfabricated Pt conductivity electrodes 12 for conductivity and temperature measurement, the later based on a PRT, and an array of exposed Pt microdisc microelectrodes 14 for the dissolved oxygen sensor 4. The conductivity sensor 6 consists of four concentric ring electrodes 12 (black in image) made from 100~300 nm thick Pt.

The PRT is made from a continuous line of 20 μm wide Pt thin film electrodes. The chips are double sided with exactly the same design for the conductivity and temperature sensors on the reverse side and are manufactured using double-sided lithography. Strain gauge effects can occur if any stress is applied to the glass substrate, bending the chips, stretching or compressing the Pt wires, and changing the PRT resistance. Using double-sided chips eliminates this effect. If one side of the PRT is stretched, increasing the resistance, the other side of the PRT will be compressed, decreasing the resistance, thereby compensating for the effect. Therefore this configuration eliminates strain gauge effects in the PRT. Strain gauge effects can be induced by water flow or the stress of the laminar material of the sensor chip. Water absorption into the laminar material, especially the SU8, can change the stress and strain gauge effects, introducing drift to the temperature sensor. Without the water barrier layer, a single-sided PRT could drift by as much as 0.1° C. due to water absorption into the SU8. This drift can be markedly reduced using the double-sided structure. It enables the sensor to be mounted vertically out form a surface. This 'fin' arrangement improves flushing and thermal contact with the water, whilst minimising thermal contact to the support/housing and hence improves the time response of the conductivity and temperature sensors. The conductivity sensor operates in the conventional four-electrode configuration with current injection from the outer electrodes and voltage measurement from the inner pair of electrodes.

Figure 4:
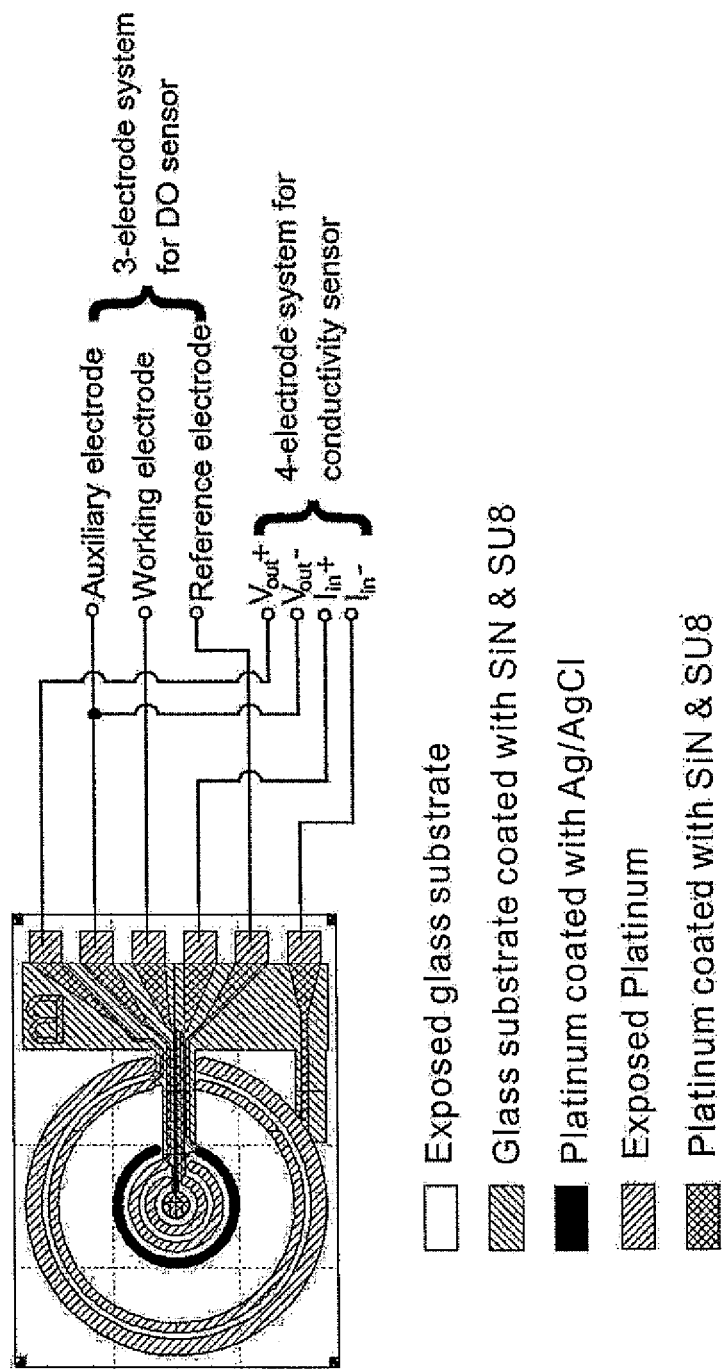
FIG. 4 shows one embodiment of the configuration of a sensor head comprising a conductivity and dissolved oxygen chip, and also showing connections to electronics apparatus.

Temperature sensing is performed on both sides of the chip, whereas conductivity is measured on the opposite side 8 to the oxygen sensor side 10. The oxygen sensor array can be formed on any platinum electrode at any location on the chip, but, as shown in FIG. 1, is preferably fabricated on the central spot electrode on one side 10 of the chip. Operation in standard two and three electrode electrochemical sensing is possible using ring electrodes not used for conductivity see FIG. 4. If sensing conductivity on one side of the double sided chip is required, then other ring electrodes can also be used. Alternatively, off chip auxiliary and reference electrodes can be used (e.g. bare wire, or gel encapsulated reference, e.g. formed from silver for a Ag/AgCl reference).

Water conductivity and oxygen diffusion coefficient is a function of temperature. As water temperature varies with location, errors can be introduced in the salinity and oxygen calculation if the water temperature around the temperature sensor is different from that around the conductivity and oxygen sensor. Advantageously, all three sensors may be integrated close together on a single substrate, minimising this temperature error.

Figure 5:
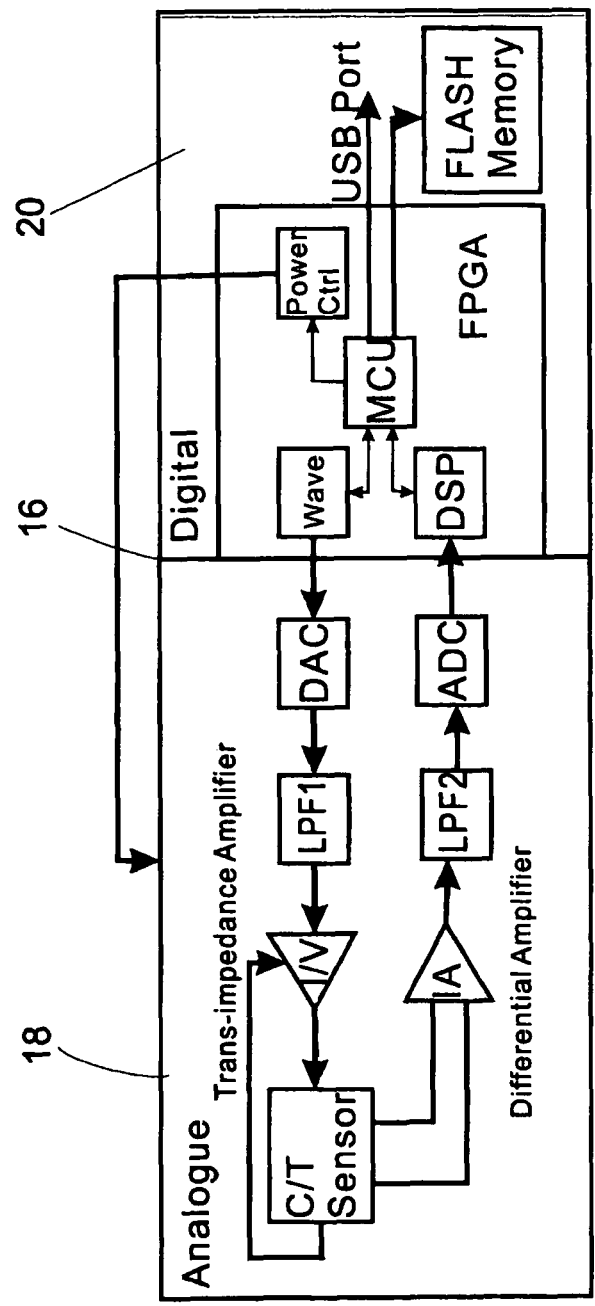
FIG. 5 shows schematically electronics for apparatus for sensing two parameters in water, namely conductivity and temperature.

An impedance measurement circuit 10 to support the conductivity and temperature sensor is shown in FIG. 5. The circuit 10 is divided into an analogue part 18 and a digital part 20. In the analogue part 18, a 16 bit/100 ksps digital-to-analogue converter (DAC) and a low pass filter LPF1 generate a sine-wave voltage signal at 1.56 kHz (100 kHz/64). A trans-impedance amplifier (I/V) is used to convert the voltage signal into current for the conductivity and temperature sensor block C/T. An instrumentation amplifier IA with high input impedance and differential interface is used to amplify the voltage response from the C/T sensor block. After removing high frequency noise using a low pass filter (LPF2), the amplified voltage response is converted into a digital signal by a 16 bit/100 ksps analogue-to-digital converter (ADC). The injection current (I) and gain of the instrumentation amplifier (G) are controlled by multiplexing the feedback resistors of the trans-impedance amplifier and the instrumentation amplifier respectively.

Both the gain of the amplifiers and the value of the feedback resistors drift with temperature and time, affecting G and I. To minimize this error, two calibration resistors with extremely low temperature coefficient (0.6 ppm/° C.) and excellent load life stability (0.005% drift after 2000 hours) are embedded in the conductivity and temperature sensor block. A 4-way multiplexer is used to select one of the conductivity and temperature sensors or the calibration resistors, and the drift error only depends on the stability of the calibration resistor. As the environment temperature varies from 0 to 30° C., these only drift by up to 0.0018%. Typically the apparatus takes 100 ms for a single channel measurement with typically a 10 second measurement interval. With this 1% load rate, the calibration resistor only drifts for 0.0002% per year and the system has a theoretical annual 0.002% drift. The calibration resistors provide a reference phase of 0° which allows the phase of the impedance to be determined by comparing the phase of the digital sine-wave from the sensor with that from the calibration resistors.

The digital part 20 of the circuit 10 performs digital signal processing, data storage, communication with a personal computer, and power management (including wake up). A low power field-programmable gate array (FPGA) (Actel IGLOO AGL600V2) with a system-on-a-chip (SOC) solution and a 64 MB flash memory are used in the digital circuit. As shown in FIG. 5, four modules are implemented in the FPGA, including a microcontroller unit module (MCU), a digital signal processing module (DSP), a waveform module, and a power control module. The waveform module is used to control the digital to analogue converter, and generates the sine-wave signal. The DSP is used to calculate the amplitude and phase of the digital sine-wave sampled by the analogue to digital converter (ADC). The power control module is used to control the power (on/off) of the analogue circuit, and the wake-up/sleep mode of the digital circuit. The MCU is used to configure the other modules, collect the processed data from the DSP, store data into the external flash memory, and communicate with the PC through a universal serial bus (USB) interface. An advantage of using a digital and analogue converter rather than a signal generator to generate the sine-wave is that the ratio between the sine-wave and digital to analogue converter sampling frequency is accurately known. Therefore a 3-parameter sine-fitting algorithm is implemented in the DSP. If this ratio were not known, the frequency would also need to be determined and such a 4-parameter algorithm would be unsuitable for real-time processing.

In a different design, the MCU is an external PIC18LF26J11 microcontroller, and the FPGA is an Actel IGLOO Nano AGLN250V2 to reduce the printed circuit board (PCB) dimension and power consumption.

The sine-fitting algorithm is similar to DC average but for AC signal with a certain frequency. Therefore the measurement noise can be reduced by increasing the sampling length and time, except the quantization noise of the DAC and ADC. A way to minimise noise is to arrange the measurement noise to be the same level as the 16-bit quantization noise (0.002% of the full scale). Typical measurement times for this condition are 100 ms; 20 ms for signal set-up and 80 ms for measurement. The circuit has an accuracy of 0.002% in amplitude and 0.02° in phase, which translates into 1 µS/cm accuracy for conductivity in the range 10~50 mS/cm, and 0.0006° accuracy for temperature in the range 0~30° C.

Figure 6:
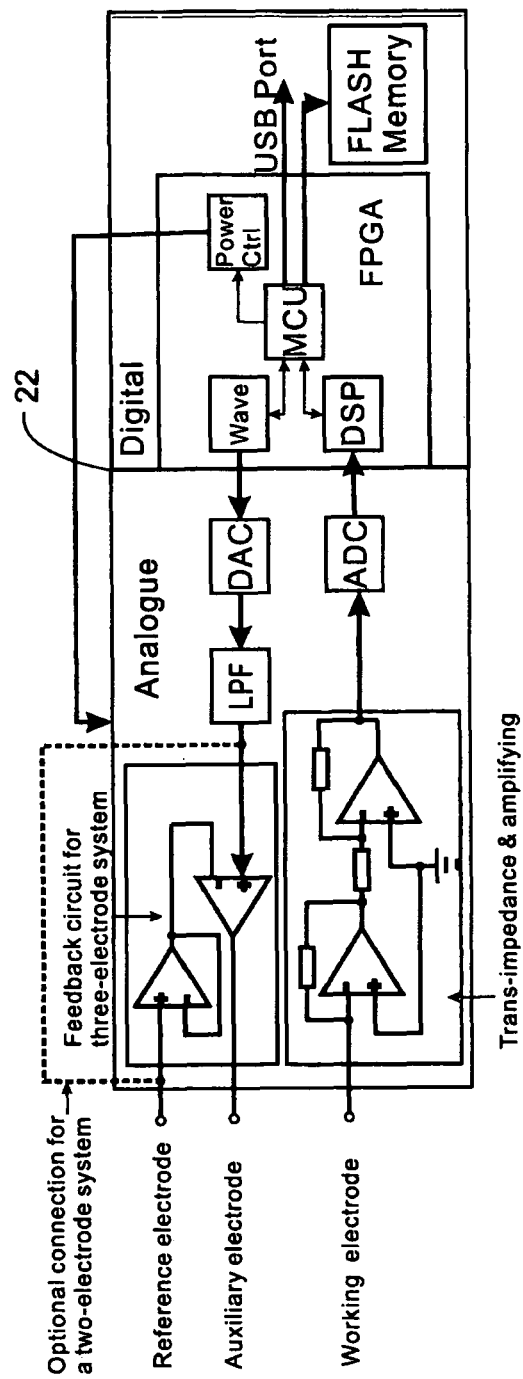
FIG. 6 is a block diagram of apparatus comprising an electrochemical water-property sensor for sensing dissolved oxygen in water, the apparatus having two/three electrodes.

FIG. 6 shows a schematic of the electronics 22 used to control and interrogate the dissolved oxygen sensor 4. Most of the electronics 22 are identical to the electronics for the conductivity and temperature sensors shown in FIG. 5, but they differ in the analogue circuit to enable either conventional two, or three electrode electrochemistry. The time response of the analogue circuit is sufficient to enable operation at high frequency (>500 kHz bandwidth). Both circuits may be implemented on a single printed circuit board or as an application specific integrated circuit.

Analogue switches are also included such that each of the electrodes can be connected to a low impedance amplifier with its output voltage set by the digital controller. This enables a digitally controlled voltage to be applied to the sensor electrodes. This is used to apply the appropriate waveforms for biofouling prevention by the electrochemical generation of chlorine (and hence hypochloric and hydrochloric acid) and if required oxygen. The electrochemical cells are formed between the platinum sensing electrodes and the Ag/AgCl or on-chip reference electrode.

Apparatus for Sensing Conductivity in Water

Referring now to FIGS. 7a and 7b, there is shown part of apparatus for sensing at least one parameter in water. More specifically, the sensed parameter is conductivity and the sensing is effected by a conductivity sensor. The sensing is effected by the use of four electrodes and the conductivity sensor is an open cell sensor which has a loop design and which has been microfabricated.

Proximity Effects

The electric field generated by the electrodes is distributed over the volume around the sensors. Therefore the cell constant will be modified if any insulating or conducting object moves into the electric field; this is the proximity effect. Proximity effects are commonly reduced by constraining the electric field inside a channel. However the use of a channel can be problematic since a continuous recirculation of the water must be ensured. The planar four electrode device has a very small leakage of field and this is shown in FIGS. 7a and 7b where four different designs were evaluated.

FIG. 7a shows diagrams of four different geometries of open conductivity cells. Cell A has two electrodes on the same side. Cell B has two electrodes on the opposite sides of the substrate. Cell C has three electrodes on the same side of the substrate. Cell D is a round electrode with a ring electrode on the same side of the substrate.

FIG. 7b shows the electric potential distributions for the four different open conductivity cells as determined by FEM simulation.

FIG. 7b also shows that, when the cell is immersed in seawater, a part of the current leaks into the surrounding water. If an object moves near the electrodes, this external current path is modified.

In a simulation, the four different cells were modelled as insulating cubes all of the same dimension (10×10×0.5 mm). The surrounding water was modelled as a sphere with a variable diameter from 10 mm to 200 mm. By comparing changes in the cell resistance as a function of the diameter of this sphere of water, the performance of the system could be estimated in terms of sensitivity to proximity effects. Less resistance change for a given change in the diameter of the water sphere means that the system has smaller proximity effects, and has better performance. The FEM simulation results are also affected by the mesh density. To minimise this, the water sphere was not placed directly around the cell. Instead, the surrounding medium was divided into several parts consisting of concentric spherical shells with diameters of 10, 20, 40, 100, and 200 mm. To simulate a water sphere of a given diameter, for example 20 mm, the medium inside the 20 mm spherical shell was modelled as water with conductivity of 60 mS/cm, while the medium outside was set to insulator. Therefore, for one cell, all simulations shared the same mesh, minimising the mesh error effect. In these simulations, media outside the certain diameter is set to be an insulator. By setting this media as a conductor, it gave the opposite effect (the same amount).

Referring to FIG. 7c, the resistance errors summarised in Table 1 show that cell D of FIGS. 7a and 7b has the best performance. This is because cell D confines the electrical potential within a small symmetric volume. When the dimension of the surrounding water is bigger than 40 mm, four times the characteristic cell dimension, the resistance of cell D is almost unchanged within a tolerance of 0.01%. This means that cell D is up to 99.99% accurate if an insulating or conducting object is 20 mm or more away from the centre of the chip. Furthermore, even if the diameter of the surrounding water is only 10 mm, which just covers the electrodes, the error is only 1.42%. Cell C (an axial symmetric design) is the second best, with error approximately twice that of cell D. Cell A and cell B have much greater proximity effects. Cell B with electrodes on the opposite sides of the substrate, does not work if the water sphere is smaller than the substrate. However, if the water sphere is bigger than the substrate, the performance of cell B is slightly better than cell A.

Apparatus for Sensing Temperature in Water

Referring again to FIG. 1, there is shown apparatus 2 for sensing at least one parameter in water. The sensed parameter is temperature and the temperature is sensed by a temperature sensor 24. The apparatus 2 includes strain relief/compensation using resistance pairs on both sides of a substrate monolith, i.e. the glass substrate 14. The temperature sensor 24 is described in more detail as follows.

Platinum Resistance Thermometer (PRT)-Bridge Temperature Sensor 24

PRTs have a higher measurement range and stability than thermocouples or thermistors, and are ideally suited for precision applications. However, the sensitivity of a PRT is relatively low. To enhance the sensitivity a bridge circuit was made, consisting of two PRTs and two precision resistors. Each platinum resistor is fabricated on each side of the glass substrate from a 20 μm wide and about 24 cm long platinum in a snake, giving a PRT with a resistance of 6.4 kohms at 20° C. Two 6.4 kohms precision resistors are soldered between the two PRT resistors to create a bridge circuit. Thin film PRTs are relatively low cost and have a fast response, although the different thermal expansion rates for the glass substrate and platinum might cause strain gauge effects, but this is hard to estimate. However, as glass is a solid material while platinum is extremely thin, the thermal expansion of the glass will dominate, and this will be proportional to temperature. The common mode strain gauge effect can therefore be ignored with little penalty, especially if the sensor is calibrated. However, strain gauge effects may still be observed if the source of strain is mechanical and differential (e.g. bending). To circumvent this problem, the PRT sensor is duplicated on the back side of the glass substrate 14, and the device is operated in differential mode to effectively eliminate the strain gauge error. This arrangement forms strain compensation means. To enhance the sensitivity of the PRT, an electric bridge consisting of two PRT resistors and two precision resistors is used as the temperature sensor 24.

Response Time

The response time of the temperature sensor 24 not only depends on the sensor chip, but also depends on the package thermal mass and water flow rate. To simulate the behaviour of the system, a FEM model was used to place a virtual sphere of water, 50 cm diameter at a temperature of 290K around the sensor. The boundary condition of the water at the surface was set to 290K and the initial temperature of the sensor head set to 289K, 1K below the surrounding water. The response time in static water can be determined by analysing how the temperature of the PRT changes with time. However, whilst the surrounding water heats the sensor package, it is also cooled by the sensor package at the same time. At the very beginning, both sensor head and the package are heated by the water, but the temperature of the sensor head grows faster, due to the higher thermal conductance of the glass, its lower thermal mass and the relativity larger contact area. At longer times, because of the bulk of the housing, together with its lower temperature, the surrounding water is cooled below the sensor head, further cooling the sensor. In static water, the cooled water surrounding the package is not refreshed by water with a higher temperature and the cooled surrounding water only receives heat by thermal conduction, which takes a long time because of the relatively low thermal conductance of the water. In flowing water, cooled surrounding water is heated by convection, so that the surrounding water temperature remains static. To simulate this situation, the temperature of the boundary is set to a constant 290K, and the sensor head is placed at a distance of 6 mm from the housing. The results are shown in FIG. 8. The sensor head takes 0.5 seconds to reach 85% change, and 2 seconds for a 99% change. Furthermore, no cooling occurs.

Oxygen Sensing

Bare disc microelectrodes are simple to manufacture, but suffer from flow sensitivity and sensitivity to changes in complex chemical media. To address these known challenges the sensor was recessed in a pit, and operated with a novel waveform that maximises sensitivity to oxygen, provides electrode conditioning to maintain performance, and shortens the measurement period. Previous recessed electrodes have been operated with sensing of the diffusion limited (steady stage current). In contrast, the apparatus of the present invention may be operated with a short measurement period compared to a longer wait (prior to measurement) and electrode conditioning cycle (after each measurement). This has a number of advantages as follows.

1. The use of a conditioning cycle maintains the condition of the electrode surface even in complex median (such as seawater) enhancing long term performance.
2. The use of a recess, for example a pit, in conjunction with a short measurement period reduces the volume of the area of depleted oxygen (the diffusion bubble) such that it remains within the recess, and this dramatically reduces flow sensitivity even at low aspect ratios.
3. The need for a large aspect ratio recess or recesses, or a membrane of reduced oxygen transmissibility, to reduce flow sensitivity is obviated. The use of low aspect ratio recesses has the advantage that it eases fabrication, increases sensitivity to oxygen, and improves time response. Flow insensitivity, and the duration of the measurement current may be improved with increased recess depth and aspect ratio, but this increases the time for oxygen to diffuse from the bulk into the recess, and therefore would decrease sensitivity whilst increasing the minimum time between valid measurements.

The design of the apparatus may be a compromise between flow insensitivity on the one hand and sensitivity and frequency of measurement on the other. In the current embodiment, the microelectrode is at the bottom of a recess of 25 µm depth and 25 µm diameter.

Apparatus Comprising a Dissolved Oxygen Sensor with Conditioning Waveform and Delay There is now described apparatus for sensing at least one parameter in water. The sensed parameter is dissolved oxygen and the dissolved oxygen is sensed by a dissolved oxygen sensor which has an electrode. The apparatus is electrode driven by a conditioning waveform and then a delay. More specifically, the electrode is driven by drive means which provides a conditioning waveform, then a wait time, and then a measurement function. The apparatus is advantageous in that the conditioning waveform is able to ensure that the apparatus operates with correct voltages, frequencies etc. An example of the conditioning waveform for the dissolved oxygen measurement is shown in FIG. 9. The conditioning waveform enables the electrode to sense the dissolved oxygen. The conditioning waveform and the wait time work together to ensure the precise and accurate functioning of the apparatus.

The apparatus may be one in which the conditioning waveform duration is 100 ms-800 ms.

The apparatus may be one in which the post conditioning waveform delay is 200 ms-1800 ms.

An important advance is that the electrode is returned to a repeatable and stable state by periodic electrode conditioning, but following this a wait period is used to return the perturbed (by conditioning) local oxygen concentration in the recess, for example the pit, to the bulk value. Then a short measurement period is used that is sufficiently short that the depleted oxygen zone (because of the reductive measurement) does not extend beyond the pit or boundary layer above the recess and hence sensitivity to flow is minimised. This is because the depleted zone does not enter the region where convective mass transfer occurs. This procedure is applied cyclically. However it should be noted that this cyclic stepped chronoamperometry is not the same as cyclic voltametry as used in other electrochemical sensor systems. The measurement (of current which is proportional to oxygen concentration) is made at a fixed voltage for short duration whereas in cyclic voltametry current is measured at a range of voltage (as voltage is swept or stepped) and these results combined or processed to calculate dissolved oxygen concentration.

Even with the waveform described above, there is some residual drift in the measurement of dissolved oxygen with time and electrode condition. To counter this, two further approaches are possible.

1. The voltage used during the measurement function may be varied over −0.019 to −0.219 V (vs the water, as the reduction voltage shown as −0.069 V in FIG. 9) and the current at the working electrode recorded at discrete voltages across this range. These current values change with time and electrode condition, but are fitted to a polynomial to give a single value that is invariant with time and electrode condition. The coefficients for the polynomial are generated through calibration at a known temperature and dissolved oxygen concentration and are subsequently applied during measurements. This calibration could be performed in situ in regions of known and stable oxygen concentration, such as the deep sea.
2. Periodically, the measurement voltage used in the waveform can be stepped over a wider range of −0.669 to 1.131 V (vs water) to generate a cyclic voltamogramme (CV). The application of this potential provides a more aggressive electrode conditioning, resetting its condition to a stable state. Following a CV, the electrode calibration returns in an approximately exponential (in time) manner (over a few hours) to a stable value. This exponential (in time) is repeatable and is characterised. Data processing is then used to remove this signal from the measurement.

The conditioning waveform duration is ideally 100 ms to 800 ms (optimised to achieve sensitivity and stability of the sensor). The post conditioning-waveform delay is ideally 200 to 1800 ms (and is a function of recess depth and tolerable flow sensitivity). Longer delays reduce flow sensitivity but reduce sample frequency. Deeper recesses require longer delay, reducing the sample frequency.

A smaller diameter and shallower recess would enable a shorter post conditioning delay, but this would reduce the sensing current and measurement duration. A shallower recess without changing the diameter would enable a shorter post conditioning delay, but this would increase the flow sensitivity. Using delays shorter than the re-equilibration time of the recess is undesirable and causes instability and or flow sensitivity.

Longer delays enable effective measurements but limit the frequency of valid measurements and reduce signal to noise ratio. Thus for example, if a measurement is required only once an hour then a delay of several minutes might be acceptable. However, to achieve maximum measurement frequency (minimum measurement period) the delay should be limited to just longer than the re-equilibration time.

The duration of the conditioning waveform may be shortened in environments where less electrode degradation occurs for example in pure laboratory media a duration of 50 ms per cycle may be sufficient. Longer durations could also be used more infrequently (e.g. conditioning every 5 seconds) but longer periods between conditioning can result in drift and loss of electrode condition. Too much cleaning results in accelerated electrode erosion (limiting lifetime) and roughening resulting in a change in the sensitivity of the sensor and hence drift. Therefore whilst the sensor, or similar sensors, may be operated outside the aforementioned ranges for high frequency continuous measurements in seawater these ranges result in optimal performance.

Apparatus Comprising an Electrochemical Water Property Sensor and Using a Biofouling Mitigation Waveform Referring to FIG. 10, there is shown an example of an antifouling waveform applied to sensing electrodes in apparatus for sensing at least one parameter in water. The parameter is sensed by at least one electrochemical water-property sensor. The sensor is such that it cleans itself by liberating chlorine. In addition the sensor could advantageously also generate oxygen.

The use of analogue switches, a low impedance amplifier, and digital control allow a wide range of voltage (and hence current) waveforms to be applied to sensing and/or antibiofouling specific electrodes on or in the vicinity of the sensor, against an Ag/AgCl reference electrode. The electrochemical generation of chlorine is particularly effective, but raising the oxygen concentration can also have advantages. Electric fields may play a role in fouling prevention/mitigation, as can alternating current.

This enables a wide range of waveforms to achieve fouling reduction. However, it may be possible to optimize the effectiveness of the waveform for particular environmental conditions. There is a trade-off between the potential and duration of applied voltage and power consumption of this fouling mitigation. Therefore waveforms should be optimized for both effectiveness and power consumption. As mentioned above, FIG. 10 shows an antifouling waveform applied to sensing electrodes. Chlorine generation is achieved by applying 2.24 V to the AgCl reference electrode driving the working electrode to >−2.56 V. Chlorine is generated from chloride at −1.36 V (vs a standard hydrogen electrode) and thus this overpotential ensures chlorine is produced. In one preferable embodiment, the current is limited by inclusion of a resistor between applied voltage and the electrode. This suppresses the electrochemical dissolution of the working electrode and increases the life of the sensor. Periodically the polarity of the applied voltage is reversed and −1.36 V applied to the reference electrode. This is primarily used to regenerate the Ag/AgCl electrode (this reaction occurs at 0.222 V vs a standard hydrogen electrode) and hence as long any suitable overvoltage is used then this is achieved. This means that the reference electrode is not consumed. During this reference electrode regeneration step, the working electrode is driven positive into the hydrogen generating region. A resting potential in the region of 0.44 V is used.

FIGS. 1-10 show apparatus for sensing a plurality of parameters in water, with different parts of the apparatus being able to sense different parameters. The different parts of the apparatus are all able to be provided in a single piece of apparatus. The single piece of apparatus may act as a miniature high precision conductivity, temperature and dissolved oxygen sensor. The apparatus may be of special use for ocean monitoring. The apparatus is manufactured using microfabrication technology. One embodiment of the apparatus may be made from platinum, patterned on a glass substrate 14. A four-electrode ring conductivity sensor may be combined with a platinum resistor temperature bridge to produce an integrated conductivity and temperature sensor. A dissolved oxygen sensor 4 (with a second temperature sensor) may be integrated onto the reverse side of the chip as shown in FIG. 1. A generic impedance measurement circuit may be used with a 3-parameter sine fitting algorithm. Conductivity and temperature accuracies may be better than ±0.01 mS/cm and ±0.005° C. respectively. The dissolved oxygen resolution may be better than 3 μm. Long-term operation in natural environments may be enhanced by the use of electrochemical generation of chlorine on the sensor electrodes themselves, which reduces the onset and affect of biofouling.

Individual components shown in the drawings are not limited to use in their drawings and they may be used in other drawings and in all aspects of the invention.

The invention claimed is:

1. A process for sensing at least one parameter in water, which process comprises:
   providing in the water apparatus comprising a dissolved oxygen sensor which is for sensing dissolved oxygen in the water and which
   has a working electrode and a reference electrode; and
   (ii) applying a voltage signal between the working electrode and the reference electrode, and such that the voltage signal provides a conditioning waveform, then a wait time that returns a perturbed local oxygen concentration at the working electrode to a bulk oxygen concentration value, and then a measurement function that is sufficiently short that the extent of a depleted oxygen zone at the working electrode is minimised, and hence sensitivity to flow is minimised.

2. A process according to claim 1 and including providing the dissolved oxygen sensor with an auxiliary electrode, and setting a voltage between the working electrode and auxiliary electrode which is such that the desired voltage between the working electrode and the reference electrode is attained.

3. A process according to claim 1 in which the conditioning waveform duration is 100 ms-800 ms.

4. A process according to claim 1 in which the wait time is 200 ms-1800 ms.

5. A process according to claim 1 and including providing a depth sensor for sensing the depth of the water.

* * * * *